United States Patent [19]

Duffett

[11] Patent Number: Plant 6,130

[45] Date of Patent: Mar. 15, 1988

[54] CHRYSANTHEMUM PLANT NAMED TOGOS

[75] Inventor: William E. Duffett, Salinas, Calif.

[73] Assignee: Yoder Brothers, Inc., Barberton, Ohio

[21] Appl. No.: 833,175

[22] Filed: Feb. 26, 1986

[51] Int. Cl.[4] ..... A01H 5/00

[52] U.S. Cl. ..... Plt./79

[58] Field of Search ..... Plt./79

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Togos particularly characterized by its flat capitulum form; decorative capitulum type; greyed-orange ray floret color; diameter across face of capitulum of up to 8 cm. at maturity; uniform nine week photoperiodic flowering response to short days; tall plant height when grown single stem, and 8 to 13 cm. peduncles on open, terminal sprays.

3 Drawing Figures

The present invention comprises a new and distinct cultivar of Chrysanthemum, botanically known as *Dentrenthema morifolium*, Ramat., previously *Chrysanthemum morifolium*, Ramat., and referred to by the cultivar name Togos.

Togos, identified as 79E31A10, is a product of a mutation induction program which had the objective of creating new Chrysanthemum cultivars that would expand the color range of an existing seedling while retaining all other original traits.

Togos was discovered and selected by William E. Duffett on Apr. 3, 1981 in a controlled environment in Salinas, Calif. as one flowering plant within a flowering block established as rooted cuttings from stock plants of the parent cultivar which had been exposed as unrooted cuttings to an X-ray source of 1600 rads.

The irradiated cultivar was an unnamed seedling, identified as 79E31010. The female parent was identified as 62422002, and was the unpatented cultivar Red Simona, previously called Firebrand. The male parent identified as 77358001 was an unnamed seedling.

The first act of asexual reproduction of Togos was accomplished when vegetative cuttings were taken from the initial selection in July of 1981 in a controlled environment in Salinas, Calif. by technicians working under formulations established and supervised by William E. Duffett.

Horticultural examination of controlled flowerings of successive plantings has shown that the unique combination of characteristics as herein disclosed for Togos are firmly fixed and are retained through successive generations of asexual reproduction.

Togos has not been observed under all possible environmental conditions. The phenotype may vary significantly with variations in environment such as temperature, light intensity and day length.

The following observations, measurements and comparisons describe plants grown in Salinas, Calif. and Littlehampton, England under greenhouse conditions which approximate those generally used in commercial greenhouse practice.

The following traits have been repeatedly observed and are determined to be basic characteristics of Togos which, in combination, distinguish this Chrysanthemum as a new and distinct cultivar:

1. Flat capitulum form.
2. Decorative capitulum type.

3. Greyed-orange ray floret color.
4. Diameter across face of capitulum up to 8 cm. at maturity.
5. Uniform nine week photoperiodic flowering response to short days.
6. Peduncle length ranging from 8 to 13 cm.
7. Tall plant height, requiring one long day week prior to short days to attain a flowered plant height of 75 to 100 cm. for year around flowerings.
8. Terminal, open spray formation.

The accompanying photographic drawings show typical inflorescence and leaf characteristics of Togos, with the colors being as nearly true as possible with illustrations of this type.

Sheet 1 is a color photograph of Togos grown as a single stem cut spray.

Sheet 2 is a black and white photograph of three views of the inflorescence of Togos.

Sheet 3 is a black and white photograph showing the upper and under sides of the leaves of Togos at three stages of development (mature, intermediate and immature).

Of the commercial cultivars known to the inventor, the most similar in comparison to Togos is Win, disclosed in U.S. Plant Pat. No. 5,108. Reference is made to attached Chart A, which compares certain characteristics of Togos to the same characteristics of Win. Similar traits are capitulum form, capitulum type and plant height. Togos has a darker ray floret color than Win, a more open spray formation than Win, and shorter peduncles.

In the following description, color references are made to The Royal Horticultural Society Colour Chart. The exact colors for the corolla of ray florets are not represented in The Royal Horticultural Society Colour Chart (R.H.S.), and the color values stated below are the closest color values to the actual color of Togos. The color values were determined on plant material grown in Salinas, Calif. on July 17, 1985.

Classification:

*Botanical.*—*Dentrenthema morifolium*, Ramat., cv Togos.

*Commercial.*—Cut spray mum.

INFLORESCENCE

A. Capitulum:

*Form.*—Flat.
*Type.*—Decorative.
*Diameter across face.*—Up to 8 cm. at maturity.

B. Corolla of ray florets:
*Color (general tonality from a distance of three meters).*—Greyed-orange.
*Color (upper surface).*—171A to 171C.
*Color (under surface).*—18A to 18B, flushed with 171C.
*Shape.*—Oblong.

Corolla of disc florets:
*Color (mature).*—4B.
*Color (immature).*—145A.

D. Reproductive organs:
*Androecium.*—Present disc florets only; scant pollen.
*Gynoecium.*—Present both ray and disc florets.

PLANT

A. General appearance:
*Height.*—Tall; 75 to 100 cm as a single stem flowering plant from a rooted cutting with 7 long days for year around flowerings.

B. Foliage:
*Color (upper surface).*—137A to 147A.
*Color (under surface).*—137C.
*Shape.*—Deeply lobed, slightly serrated.

CHART A

COMPARISON OF TOGOS AND WIN

| CULTIVAR | RAY FLORET COLOR | CAPITULUM FORM AND TYPE | SPRAY FORMATION |
|---|---|---|---|
| TOGOS | GREYED-ORANGE | FLAT DECORATIVE | TERMINAL OPEN |
| WIN | ORANGE BRONZE | FLAT DECORATIVE | TERMINAL UPRIGHT |

| CULTIVAR | DIAMETER ACROSS FACE OF CAPITULUM | PLANT HEIGHT | FLOWERING RESPONSE PERIOD |
|---|---|---|---|
| TOGOS | UP TO 8 CM. | TALL | NINE WEEKS |
| WIN | 80 to 100 mm. | TALL | TEN WEEKS |

COMPARISONS MADE OF PLANTS GROWN AS SINGLE STEM SPRAY CUT MUMS IN SALINAS, CALIFORNIA

I claim:

1. A new and distinct Chrysanthemum plant named Togos, as described and illustrated, and particularly characterized as to uniqueness by the combined characteristics of flat capitulum form; decorative capitulum type; greyed-orange ray floret color; diameter across face of capitulum of up to 8 cm. at maturity; uniform nine week photoperiodic flowering responses to short days; tall plant height when grown single stem, and 8 to 13 cm. peduncles on open, terminal sprays.

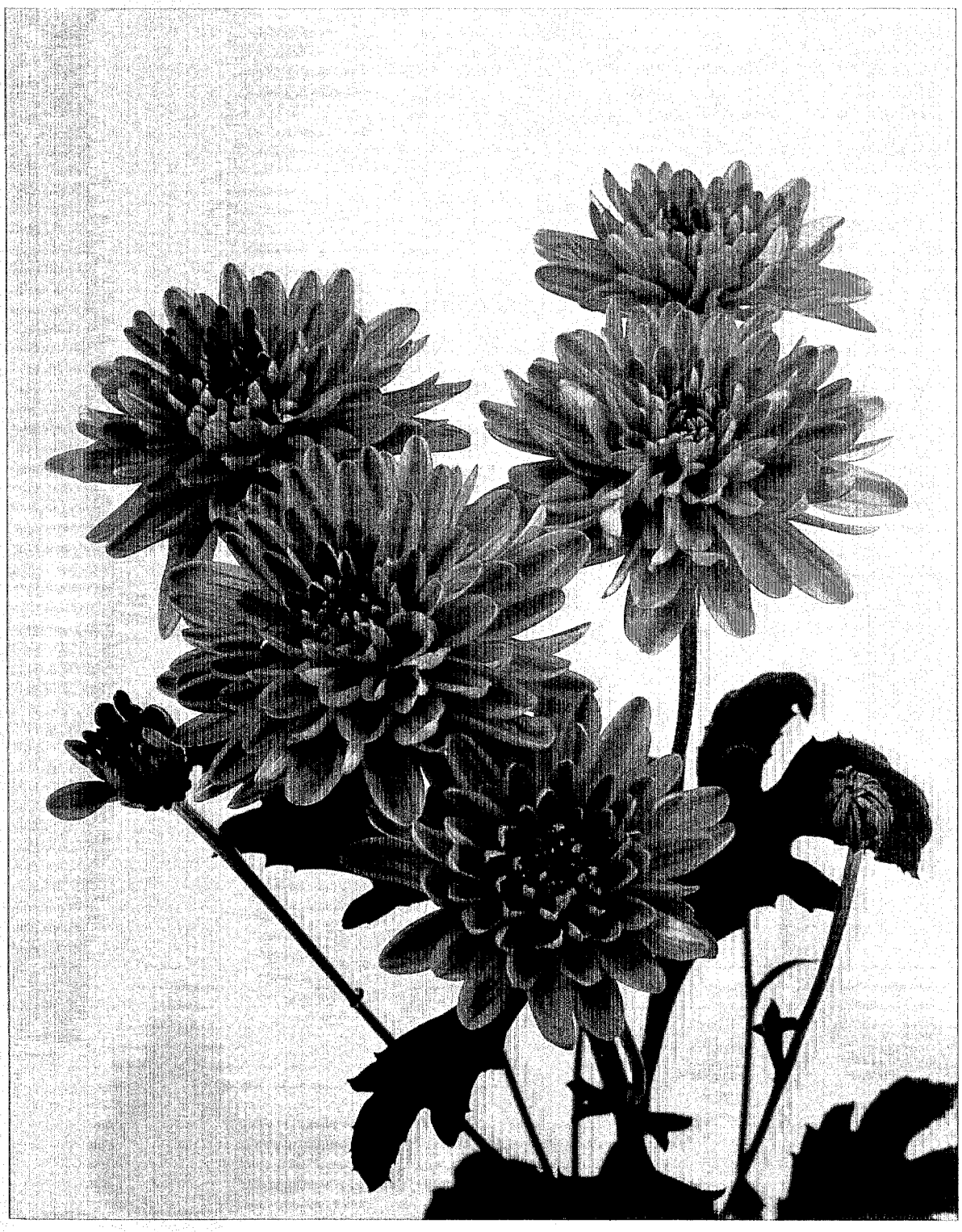

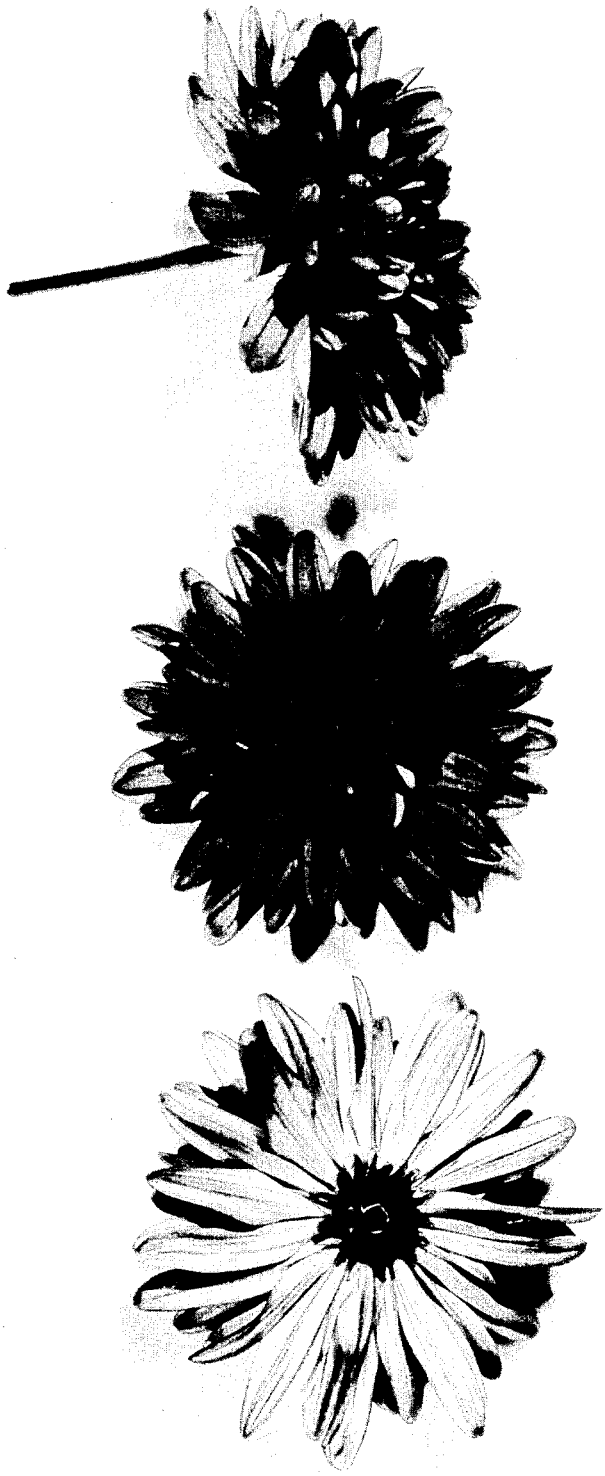

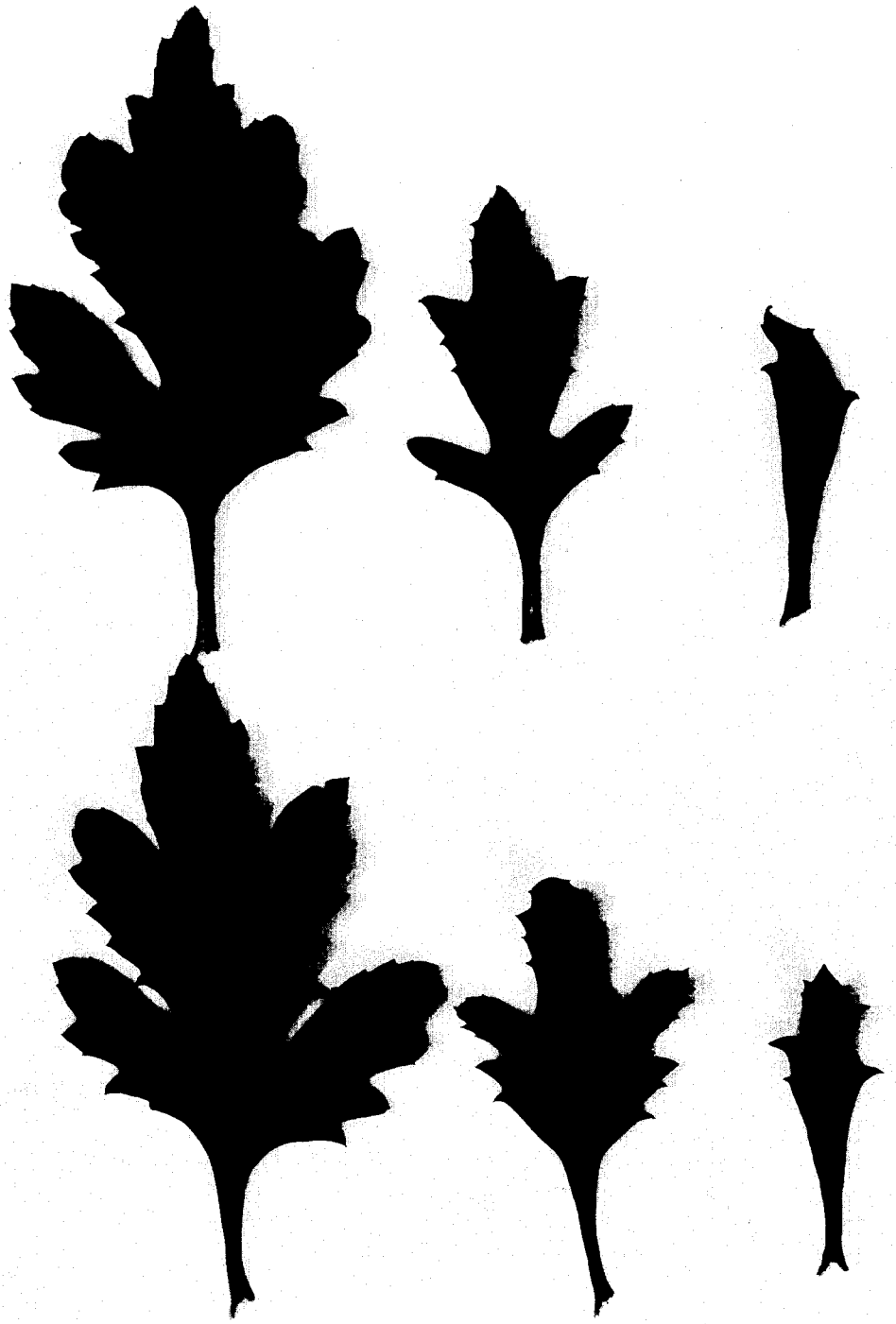

* * * * *